United States Patent [19]

Olinger et al.

[11] Patent Number: 5,204,115
[45] Date of Patent: Apr. 20, 1993

[54] DIRECTLY COMPRESSIBLE XYLITOL AND METHOD

[75] Inventors: Philip M. Olinger, Schaumburg, Ill.; Auli Karhunen, Jokioinen, Finland

[73] Assignee: Suomen Xyrofin Oy, Kotka, Finland

[21] Appl. No.: 626,495

[22] Filed: Dec. 12, 1990

[51] Int. Cl.⁵ .......................... A61K 9/16; A61K 9/28
[52] U.S. Cl. .................. 424/470; 424/499; 424/440
[58] Field of Search ............... 424/464, 470, 487, 499, 424/440

[56] References Cited

U.S. PATENT DOCUMENTS

| | | | |
|---|---|---|---|
| 3,042,531 | 7/1962 | Leal et al. | 99/141 |
| 4,013,775 | 3/1977 | Nelson et al. | 426/285 |
| 4,292,337 | 9/1981 | Andersen et al. | 426/573 |
| 4,405,647 | 9/1983 | Fisher et al. | 426/4 |
| 4,569,852 | 2/1986 | Yang | 426/534 |
| 4,572,916 | 2/1986 | Lindley et al. | 514/777 |
| 4,680,189 | 7/1987 | Schumacker | 426/285 |
| 4,753,805 | 6/1988 | Cherukuri et al. | 426/5 |
| 4,882,154 | 11/1989 | Yang et al. | 424/440 |
| 4,980,169 | 12/1990 | Oppenheimer et al. | 424/439 |

OTHER PUBLICATIONS

Connine et al., "Preparation of Small Solid Pharmaceutical Spheres" D&CI 1970.
Remington's Pharmaceutical Sciences, Mack Publishing Co. 18th Edition (1990).

Primary Examiner—Thurman K. Page
Attorney, Agent, or Firm—Baker & McKenzie

[57] ABSTRACT

A directly compressible xylitol granulate comprising xylitol and a physiologically acceptable, non-cariogenic binder taken from the group consisting of polymerized reducing sugars, an alkali carboxymethylcellulose and hydrogenated starch hydrolysate. The granulate is directly compressible and exhibits the taste profile, metabolic and cariostatic properties of xylitol.

37 Claims, No Drawings

DIRECTLY COMPRESSIBLE XYLITOL AND METHOD

I. INTRODUCTION

This invention relates to a directly compressible xylitol granulate. The granulate comprises xylitol and a physiologically acceptable, non-cariogenic binder taken from the group consisting of polymerized reducing sugars, an alkali carboxymethylcellulose, and hydrogenated starch hydrolysate, and combinations thereof, binders which do not detract from the taste profile of xylitol; polydextrose is a preferred polymerized reducing sugar, and sodium carboxymethylcellulose is a preferred alkali carboxymethylcellulose. The invention also relates to a method of producing a directly compressible xylitol granulate which can be used in tabletting contexts, and to tablets which contain xylitol as a sweetening agent which exhibit high hardness, low friability, are non-cariogenic and exhibit a noted cooling effect when consumed.

II. BACKGROUND OF THE INVENTION

A. The Advantages of Xylitol

The most commonly used sweetener for food and pharmaceutical contexts is sucrose. Sucrose is used for its well-known sweetening properties and also for bulking purposes. Although a wide variety of alternate sweeteners are available, sucrose is generally considered to be the optimum sweetener with regard to taste profile and technological properties. However, sucrose has been implicated as a contributory factor in many diseases including hypertension, coronary heart disease, arterial sclerosis and dental caries. These health concerns have led health care professionals to analyze the effects of sucrose and its prominent role in the diet.

Perhaps the most significant, well-documented effect of sucrose is its contribution to tooth decay. The mouth contains a number of bacterial strains which ferment common dietary carbohydrates such as sucrose. This fermentation generates acid as an end product which lowers the pH in the mouth; the lowered pH leads to a demineralization of tooth enamel and finally to the formation of dental lesions or caries.

It is well known that it is not the total quantity of sugar consumed per se, but the frequency of consumption that contributes to dental caries. Thus, the presence of sucrose and other fermentable carbohydrates in regular meals is not the principal cause of tooth decay. The consumption of fermentable carbohydrates between meals in the form of confections and sweetened pharmaceuticals (and the frequency of such consumption) have been shown to have a close relationship to the formation of dental caries. Long after the candy or drug has been consumed, the fermentable carbohydrate stays in the mouth and is fermented by *Streptococcus mutans* and other cariogenic bacteria, lowering the mouth pH and promoting dental caries as described above.

One approach to fighting dental caries is to reduce or eliminate the amount of fermentable carbohydrates such as sucrose in pharmaceutical or food contexts. The replacement of fermentable carbohydrates by sugar substitutes which cannot be fermented, or are less easily fermented by *S. mutans* and other bacteria has been shown to decrease the development of dental caries.

Xylitol has been used as a sugar substitute in certain contexts (e.g. chewing gum: U.S. Pat. No. 4,514,422 (Yang) and 3,422,184 (Patel)) with practical and commercial success. The use of xylitol is attractive because of its taste and technological advantages. Xylitol is a naturally occurring five carbon sugar alcohol which has the same sweetness as sugar and a caloric content which is less than that of sugar. Xylitol is found in small amounts in many fruits and vegetables and is produced in the human body during normal metabolism. Xylitol is particularly attractive because of its known metabolic, dental and technical characteristics.

From a metabolic perspective, xylitol is metabolized largely independent of insulin, so it can be safely consumed by non-insulin dependent diabetics. Further, xylitol has been shown to delay gastric emptying and to possibly suppress food intake which means it may have an important role in weight reducing diets.

A significant advantage of xylitol is that it is not fermented by *S. mutans* and other bacteria found in the mouth and, therefore, does not produce acids which, as described herein, contribute to the formation of dental caries. Xylitol is well established as a non-cariogenic substance, i.e. xylitol does not contribute to caries formation. Significant data also exists which supports the view that xylitol is not only non-cariogenic, but actively suppresses the formation of new caries and may even reverse existing lesions by inducing remineralization, i.e. it is a cariostatic material. A summary of clinical data regarding the effects of xylitol and its possible mechanisms is set forth in Bar, Albert, *Caries Prevention With Xylitol: A Review of the Scientific Evidence*, 55 Wld. Rev. Nutr. Diet. 183-209 (1983). The mechanism or mechanisms by which xylitol effects any cariostatic properties is not yet known, but some possible mechanisms which have been suggested include a reduction of oral levels of *S. mutans*, a reduction in the development of plaque, the stimulation of the flow of protective saliva, the favorable alteration of the composition of saliva, the retardation of demineralization and an enhancement of remineralization of tooth enamel.

Xylitol also has significant technological advantages, particularly with respect to taste profile. Xylitol produces a pleasant cooling effect in the mouth when consumed in the crystalline state. The energy required to dissolve one gram of xylitol is 34.6 calories, the highest known value for sugars and sugar alcohols; this produces a physical cooling effect which is desirable in many contexts. Xylitol is as sweet as sugar and does not typically manifest unpleasant aftertastes.

Other polyols, such as sorbitol, mannitol, lactitol and others have also been substituted for sucrose in a variety of contexts. All of these polyols have certain advantages—such as non-cariogenicity—over sucrose. However, none of the other polyols have been demonstrated to have a cariostatic effect.

One context in which xylitol has been heretofore utilized with only limited success is as a constituent in tablets. In pharmaceutical contexts, tablets are used for bringing active substances into a size, shape and texture that can be dosaged, chewed, sucked, swallowed whole or dissolved in water for drinking. In food contexts, tablets can take the form of compressed, fruit or mint flavored confections which consist of a sweetener(s), flavor(s) and optionally color and acid. Because of its taste and cariostatic properties as described above, xylitol is a potentially attractive constituent in tablets for both food and pharmaceutical purposes Other polyols have been utilized in tablet contexts as diluents, flavoring agents and binders, but xylitol has not heretofore been used extensively in this context.

Sweetness in pharmaceutical tablets fulfills the purpose of making the product more pleasant to eat and to mask any unpleasant taste of the active ingredient(s). Today, many pharmaceutical tablets are sweetened with sucrose, lactose and other fermentable carbohydrates which are also used as diluents. Replacing sucrose and other fermentable carbohydrates with xylitol in those applications which must be sweetened would eliminate the use of cariogenic formulations in medicaments such as throat lozenges, cough tablets, vitamins, chewable tablets and others, and also takes advantage of the other attributes of xylitol discussed above, such as its noted cooling effect and metabolic characteristics.

In food contexts, tablets are usually sucked or chewed by the user and are often used as breath mints. Sucrose is the sweetener of choice in these contexts and has bulking properties as well. Replacing sucrose with xylitol would enable tablets to exploit the unique advantages of xylitol, particularly its anti-caries properties, and its pronounced cooling effect.

The cariostatic effect of xylitol is particularly important because clinical studies have shown that it is not the quantity of sucrose (or other acid producing substances such as maltose, lactose and dextrose), but the frequency of sucrose intake that is critical for caries development. Many pharmaceutical and food tablets are designed to be and are consumed at frequent and/or regular intervals throughout the day. For this reason, some dental researchers have suggested switching from sucrose, maltose, lactose, dextrose to a non-acid producing sweetener such as xylitol in pharmaceutical and food contexts.

B. Tableting Techniques and Tablets

Tablets can be formed by compression or by molding. Simple compression techniques have been known for centuries; in 1577 Hieronymous Bosch, in his *Kreuttenbuch*, describes a simple press, used for making medicines. The sugar coating of "pills" was first attributed to Jean de Renou in 1606, and one of the first patents for the manufacture of "pills and medical lozenges" was granted to one Thomas Brockedon in Great Britain in 1843. Many types of tablets exist including chewable tablets, lozenges, effervescent, coated centers, film coated tablets, enteric coated tablets, time release tablets (for release of ingredients over time) multi-layered tablets and others.

Modern compression tableting techniques—irrespective of the type (and ultimate shape of the end product)—utilize a piston like device with three stages in each cycle: (1) filling —adding the constituents of the tablet to the compression chamber; (2) compression—forming the tablet; and (3) ejection—removing the tablet. The cycle is then repeated. A representative tablet press is a MANESTY Novapress, manufactured by Manesty Machines Ltd., Liverpool, England, and many others are available.

In order to make tablets, preferably all ingredients—or at least the carrier or diluent which typically makes up the bulk of the tablet—must have certain physical characteristics, including the ability to flow freely, and acceptable cohesion (or compressibility). Because many materials have some, or none, of these qualities, techniques must be developed to impart these characteristics to the constituents. In this context, free flowing means that the particles to be compressed must enter the compression chamber as discreet particles; compressible means the particles form a tablet after compression and do not remain in a powdered or substantially powdered form.

Two critical criteria in the quality of a tablet are crushing strength (or hardness) and friability. The resistance of the tablet to chipping, abrasion, or breakage under conditions of storage, transportation and handling before usage depends on its hardness. Hardness is measured by determining lateral breaking strength (expressed in kilo pounds or Strong Cobb Units wherein 1 kp=1.4 S.C.U.) exerted on a single tablet at the moment of rupture. A representative hardness tester is the Model HT-300 manufactured by Key International, Inc. Acceptable hardness depends on the desired mouthfeel and the expected end use and packaging conditions of the tablet, but in most contexts, tablet hardness must be greater than about 10 S.C.U. to be commercially useful.

Friability is also a standard test known to one skilled in the art. Friability is measured under standardized conditions by weighing out a certain number of tablets (generally 20 or more), placing them in a rotating plexiglass drum in which they are lifted during replicate revolutions by a radial louver, and then dropped through the diameter of the drum. After replicate revolutions, the tablets are reweighed and the percentage of powder "rubbed off" or broken pieces is calculated. Friability in the range of about 0% to 3% is considered acceptable for most drug and food tablet contexts. Friability which approaches 0% is particularly preferred.

Tablets of insufficient hardness exhibit capping and/or lamination and can easily break apart or disintegrate under normal handling and packaging conditions. Tablets of insufficient hardness cannot be used for lozenges or mints which are designed to be sucked in the mouth, releasing the active ingredient(s) or flavor over time, and may have an undesirable powdery, grainy or coarse mouthfeel.

C. Use of Xylitol in Tablet Contexts

Xylitol is not considered to be directly compressible, i.e. crystalline xylitol cannot be compressed into tablets of sufficient hardness and low friability. Therefore, in order to utilize xylitol in tablets, a variety of approaches to impart these characteristics have been used, without complete success.

One method has been to compress xylitol into tablets of relatively low initial hardness (e.g. about 6 S.C.U.) and "finish" the outer surface. The finishing step takes advantage of the unique crystallization properties of xylitol and its low melting point. Basically, the compressed tablets—which have a low initial hardness—are heated by exposing the surface of the tablets to hot air at temperatures greater than 94° C. which cause a phase change in the xylitol from solid to liquid. After cooling, recrystallization occurs quickly and a "glass" hard surface layer is formed. This finishing step, however, adds another significant step to the production process (thereby increasing the cost and decreasing the efficiency), cannot be used in all tablet contexts, and does not result in a tablet with uniform hardness.

Xylitol has also been admixed with other polyols to form a mixture which is then compressed. U.K. Patent No. 1,526,020 discloses a method for the production of compressed tablets wherein xylitol is dry blended with another polyol (e.g. sorbitol, mannitol, maltitol) so that the xylitol is present in about 10–90% by weight in the final product. However, the use of a xylitol/additional polyol blend can create disadvantages. The use of crystalline xylitol produces tablets which are too coarse in many contexts. The use of milled xylitol (less than 200 micron average particle size) produces a dry blended product (with sorbitol, for example) wherein flowability of the blend is extremely poor (near zero). Tableting machinery equipped with a force feeder is required. Because this is not a desired characteristic, use of milled xylitol in conjunction with another polyol is not a viable commercial alternative. A granulated form of xylitol would be much preferred.

Finnish Patent Appln. No. 880892 filed Feb. 25, 1988 discloses the use of a granulate which comprises xylitol in the range of about 94% to about 98% by weight and another physiologically acceptable polyol which serves as the binder in the range of about 1–5% by weight. The granulate can be compressed to form tablets, but although the mouthfeel, initial hardness and friability is improved over tablets made from crystalline xylitol, it is not acceptable for some commercial applications, and the granulate must be prepared under controlled conditions to prevent attack by atmospheric moisture.

Additional work has been done with xylitol granulates. Granulation is a process carried out today by various methods including fluidized bed techniques, centrifugal fluidizing, compacting and vacuum techniques. Granulation requires the use of a "binder" which assists in formulation of granules, i.e. it brings the particles into a granulated, free flowing form. Binders which are often used include starch, gelatin, sugars such as sucrose, dextrose, and lactose, natural and synthetic gums, microcrystalline cellulose and others.

These binders are not necessarily particularly acceptable for use with xylitol because they may impair or eliminate the taste, cariostatic, metabolic and other properties of xylitol which make it an attractive constituent of pharmaceutical and food tablets. Some binders, including gum arabic, if utilized as a binder for xylitol, will reduce the perceived cooling effect of xylitol created by xylitol's significant negative heat of solution. Other binders may impart a nondesired and unacceptable mouthfeel. Gelatin, if used as a binder, in addition to masking the cooling effect of xylitol, may not be desired for ethnic reasons. Starches and other cariogenic fermentable carbohydrates, if utilized as binders, are not desired because of their negative impact on oral health.

It has now been discovered, surprisingly and unexpectedly, that certain compounds such as polymerized reducing sugars like polydextrose, alkali carboxymethylcellulose and hydrogenated starch hydrolysate when used as binders produce a directly compressible xylitol granulate which can be compressed to tablets of high hardness and low friability and yet allow the full range of xylitol's taste, cariostatic and other properties to be expressed in a tablet context. Use of these binders will allow, for the first time, the use of xylitol in large scale, commercial tableting processes to produce pharmaceutical and food tablets sweetened with xylitol, tablets that exhibit remarkable hardness, low friability that in some cases approaches zero, excellent taste profile, and are non-cariogenic and potentially cariostatic.

SUMMARY OF THE INVENTION

The present invention contemplates a directly compressible, non-cariogenic xylitol granulate which comprises xylitol and a binder in the range of about 0.1% to about 5% by weight, wherein the binder is physiologically acceptable, non-cariogenic and is taken from the group consisting of polymerized reducing sugars, alkali carboxymethylcellulose and hydrogenated starch hydrolysate. Binders which are particularly preferred are polydextrose, in a partially purified or purified and/or a partially neutralized or neutralized form, and sodium carboxymethylcellulose. The use of a polydextrose binder in the range of about 0.5% to about 5% by weight is preferred, with polydextrose present in the amount of about 3% by weight being particularly preferred. The use of a sodium carboxymethylcellulose binder in the range of about 0.5% to about 3% by weight is preferred, with sodium carboxymethylcellulose present in the amount of about 1.5% by weight being particularly preferred. The use of hydrogenated starch hydrolysate in the amount of about 1% to about 5% by weight is preferred, with hydrogenated starch hydrolysate present in the amount of about 3% by weight being particularly preferred.

The invention also contemplates a directly compressible xylitol granulate which additionally includes an intense sweetener. Intense sweeteners taken from the group consisting of dipeptide sweeteners, saccharin, acesulfame K, stevioside, cyclamates, neohesperidin dihydrochalcone and sucralose are preferred.

The invention also contemplates a relatively stable, non-cariogenic consumable tablet which exhibits a noted cooling effect, a tablet which is sweetened with a granulate which comprises xylitol in the range of about 90% to about 99% by weight, and a physiologically acceptable non-cariogenic binder taken from the group consisting of polymerized reducing sugars, alkali carboxymethylcellulose and hydrogenated starch hydrolysate in the range of about 0.1% to about 5% by weight, wherein said tablet exhibits hardness of at least 10 Strong Cobb Units and a friability of less than about 3%. A tablet which exhibits hardness of at least 10–40 Strong Cobb Units and a friability of less than about 1% is particularly preferred. Particularly preferred binders include polydextrose in a partially purified or purified, and/or partially neutralized or neutralized form, and sodium carboxymethylcellulose. A consumable tablet wherein said tablet is sweetened with a granulate comprising about 97% xylitol and about 3% polydextrose by weight is particularly preferred. A consumable tablet wherein said tablet is sweetened with a granulate comprising about 99.5% to about 97% by weight xylitol and about 0.5% to about 3.0% by weight sodium carboxymethylcellulose is preferred, with a granulate comprising about 98.5% xylitol and about 1.5% by weight sodium carboxymethylcellulose being particularly preferred.

A consumable tablet wherein said tablet is sweetened with a granulate comprising about 95% to about 99% xylitol and about 1% to about 5% hydrogenated starch hydrolysate by weight is preferred, with a granulate comprising about 97% xylitol and about 3% hydrogenated starch hydrolysate being particularly preferred.

The invention also contemplates a consumable tablet which additionally includes an intense sweetener. A particularly preferred intense sweetener is taken from the group consisting of dipeptide sweeteners, saccharin, acesulfame K, stevioside, cyclamate, neohesperidin dihydrochalcone and sucralose.

The invention also contemplates a method for the production of a directly compressible, non-cariogenic xylitol granulate which consists of granulating milled xylitol with an average particle size of between about 40 to about 180 microns (with an average particle size of between about 40 to about 120 being preferred) with a physiologically acceptable, non-cariogenic binder taken from the group consisting of polymerized reducing sugars, alkali carboxymethylcellulose and hydrogenated starch hydrolysate in the range of about 0.5% to about 5% by weight and screening the resulting granulate. In one method, an aqueous binder solution is added to milled xylitol, and the resulting granulate is dried and screened. Milled xylitol with an average particle size of between about 50 and about 90 microns is particularly preferred. Polydextrose, in a partially purified or purified and/or partially neutralized or neutralized form, sodium carboxymethylcellulose and hydrogenated starch hydrolysate are particularly preferred binders.

The invention also contemplates a directly compressible granulate which comprises a polyol such as mannitol, lactitol, sorbitol, isomalt and maltitol or a sweetener suitable for diabetic applications such as crystalline fructose and/or mixtures thereof, and a polydextrose binder present in the range of about 0.1% to about 5% by weight. A sweetener suitable for diabetic applications is one which has a glycemic index of less than 50 based upon comparative blood glucose response relative to glucose ingestion. See Jenkins et al., "Glycemic Index of Foods: A Physiological Basis for Carbohydrate Exchange", 34 *The American Journal of Clinical Nutrition,* 362 (March 1982) for methodology.

DETAILED DESCRIPTION OF THE PREFERRED EMBODIMENT

A. General

The granulate of the present invention exhibits excellent flowability and compressibility when used in typical tableting equipment, such as a Manesty Betapress or other tableting presses which are known to one of ordinary skill in the art. The xylitol used to form the granulate is xylitol milled to an average particle size of between about 40 to about 180 microns. Crystalline xylitol can be milled, ground or otherwise comminuted to reach the preferred particle size.

The binder contemplated by the present invention is a physiologically acceptable, non-cariogenic binder. Surprisingly and unexpectedly, polydextrose—a polymerized reducing sugar—functions as an excellent binder in this context; polydextrose has heretofore been utilized solely as a bulking agent for use in baked goods, baking mixes, frozen desserts, pudding, chocolate, hard candy and soft candy and has not been utilized as a binder in the pharmaceutical or compressed candy contexts. Polydextrose is available from the Pfizer Chemical Division, New York, N.Y. Polydextrose is a water-soluble, randomly bonded condensation polymer of dextrose, containing minor amounts of bound sorbitol and citric acid. Polydextrose is available in four forms: (1) polydextrose type "A"; (2) polydextrose type "N" (which contains some free acid in liquid form); (3) polydextrose "K" (a partially neutralized version which is treated with sodium carbonate to diminish the acidity of the polydextrose); (4) "new" polydextrose, a purified version of polydextrose type "A". Other physiologically acceptable, non-cariogenic polymers of reducing sugars may also function as binders in this context.

Another binder is an alkali carboxymethylcellulose such as sodium carboxymethylcellulose. Sodium carboxymethylcellulose can be utilized in a wide range of cosmetic, food, pharmaceutical and industrial applications, but has heretofore not been utilized as a binder with xylitol in tableting contexts. Sodium carboxymethylcellulose is available from Aqualon Company, Wilmington, Del. Sodium carboxymethylcellulose is a cellulose ether produced by reacting alkali cellulose with sodium monochloroacetate under controlled conditions. Sodium carboxymethylcellulose is available in food, pharmaceutical and standard grades with varying degrees of substitution (from 0.38 to 1.4) and viscosity characteristics in solution with water.

A further binder is hydrogenated starch hydrolysate. Hydrogenated starch hydrolysate is the catalytically hydrogenated product of high maltose syrup and is commercially available from a wide variety of sources.

Granulation of the xylitol and binder can be achieved with any of the standard means of granulation available. In bench type applications, milled xylitol is combined with polydextrose syrup, mixed in a blender, sieved and dried. The dried granulate is further sieved to produce particles of uniform size and shape.

Suitable commercial granulators or granulating systems include the Lodige horizontal blender (Gebruder Lodige GmbH) in combination with a fluidized bed dryer, the Glatt vertical fluidized bed granulator (Glatt GmbH, Binzen, West Germany), the Aeromatic vertical fluidized bed granulator (Aeromatic AG, Bubendorf, Switzerland) and the Schugi granulator (Schugi, BV, Lelystad, Holland). Other granulation devises commonly known to those skilled in the art can be utilized in the practice of our invention.

The produced and dried granulate is usually screened following the granulation step to remove coarse particles. A suitable sieve size for this purpose is a 16 mesh (1.2 mm) screen. The coarse particles can either be reworked, milled or dissolved for further use.

The granulate can be utilized as a sweetening, flavor or bulking agent and/or as a diluent in food and pharmaceutical contexts alone, or in combination with other sweeteners (such as intense sweeteners), other polyols and/or other binding agents.

B. Experimental

Example 1

Laboratory Scale Production of Directly Compressible Granulate 500 grams of milled, 90 micron xylitol was served into a HOBART N-50 blender and mixed at the slowest speed for 30 seconds. A 50% solution of polydextrose K (Pfizer) was added slowly during mixing, the mixing speed increased to intermediate and then continued for 30 seconds. The resulting granules were sieved through a 120 mesh (125 micron) sieve and dried in a BRUCK'S drying drum at 30 rpm for 15–60 minutes, and then overnight at 40° C. in a drying cabinet. The dried granules were sieved again through a 120 mesh (125 micron) sieve. A granulate with good flowability which was not excessively lumpy, sticky or moist was produced.

The granulate was formed into tablets by mixing the granulates with 1% Magnesium stearate (a lubricator) in a TWIN SHELL dry blender (Patterson-Kelly Co.) for 3 minutes. Tablets were made using a KORSCH tableting machine at forces of 9.4, 20 and 32.0 kN. The resulting tablets exhibited crushing strengths of about 10, 17 and 14 Strong Cobb Units at the respective compression forces of 9.4, 20 and 32.0 kN. Each tablet exhibited a good finish and a pleasing sweetness and cooling sensation.

Example 2

Production of a Directly Compression Xylitol Granulate 6,000 grams of xylitol milled to an average particle size of 50 microns was charged into a type FKM 50 Lodige horizontal blender and mixed at a rate of 60 rpm. 528.6 grams of a polydextrose syrup comprising 35% Polydextrose K (dry basis) and water was sprayed into the Lodige over a five minute period (105.7 g/min). The resulting wet granulate was mixed for an additional five minute period and then mixed with the Lodige chopper for an additional minute. The resulting admixture was then placed in a Glatt vertical bed fluidized drying system and dried to a product temperature of 50° C. to generate a granulate with a moisture level of less than about 0.5% by weight. The granulate was then screened through a 16 mesh sieve with the resulting overs being segregated for further processing. The resulting granulate exhibited good flow properties.

The granulate (1,980 g) was mixed with magnesium stearate (20 g) for three minutes and compressed into 500 mg tablets (7/16 inch diameter utilizing a Manesty Betapress) and ¼ inch precompression at 2.5 tons compression force. The resulting tablets exhibited an initial hardness of 15.5 Strong Cobb Units and a 24 hour hardness of 24.4 Strong Cobb Units. Tablet friability was less than 2%. Each tablet exhibited a good finish, was free of capping or lamination and was observed to have a pleasing sweetness and cooling sensation.

Example 3

Production of a Directly Compressible Xylitol Granulate 6,000 g of xylitol milled to an average particle size of 50 microns was charged into a GPCG 5/9 Glatt vertical fluidized bed granulator. 1,856 g of a polydextrose syrup comprising 10% Polydextrose K (dry basis) and water was sprayed onto the xylitol over a 20 minute period (92.8 g/min) at 2.5 bar pressure utilizing a 2 mm nozzle located in the middle of the fluidized bed. The Glatt was operated in the WSG mode wherein the polydextrose syrup was applied for 60 seconds and terminated for 4 seconds of dust collector shaking. The granulate was dried to a product temperature of 50° C. to generate a granulate having about 0.2% moisture by weight. The granulate was then screened through a 16 mesh sieve with the resulting overs being segregated for further processing. The resulting granulate exhibited good flow properties. It had a bulk density of 0.47 g/ml and an average particle size of about 350 microns. The granulate was further characterized in that less than 10% of the product was less than 149 microns. The granulate contained about 3% polydextrose by weight.

The granulate (5,529 g) was mixed with magnesium stearate (55.8 g) for a period of 3 minutes and compressed as described in Example 2 into 550 mg tablets. The resulting tablets exhibited a hardness of about 18 Strong Cobb Units. Tablet friability was 0.2%. Each tablet exhibited a good finish, was free of capping or lamination and was observed to have a pleasing sweetness and cooling sensation.

Example 4

Production of a Directly Compressible Xylitol Granulate 6,000 g of xylitol milled to an average particle size of 90 microns was granulated with Polydextrose K as described for Example 3. The resulting granulate exhibited good flow properties. It had a bulk density of 0.53 g/ml and an average particle size of about 350 microns. Less than 5% of the final product passed through a 177 micron sieve. The granulate contained about 3% polydextrose and about 0.6% water by weight.

Tablets were prepared as described in Example 3. The resulting tablets exhibited a hardness of 18 Strong Cobb Units. Tablet friability was 0.3%. Each tablet exhibited a good finish, was free of capping or lamination and had a pleasing sweetness and cooling effect.

Example 5

Production of a Directly Compressible Xylitol Granulate 6,000 mg of xylitol milled to an average particle size of 50 microns was granulated with Polydextrose K utilizing 1,163 g of a 5.12% solids Polydextrose solution in water as described for Example 3. The resulting granulate exhibited good flow characteristics. It had a bulk density of 0.44 g/ml and an average particle size of about 300 microns. Less than 10% of the screened produced passed through a 149 micron sieve. The granulate contained about 1% polydextrose.

Tablets were prepared as described in Example 3. The resulting tablets exhibited a hardness of 21 Strong Cobb Units. Tablet friability was about 3%. Each tablet exhibited a good finish and was observed to have a pleasing sweetness and cooling sensation.

Example 6

Production of a Directly Compressible Xylitol Granulate 7,000 g of xylitol milled to an average particle size of 50 microns was granulate with Polydextrose K utilizing 2,455 g of a 5% solids polydextrose solution in water as described for Example 3. The nozzle opening was reduced to 1.2 mm and the Polydextrose solution was sprayed at 3 bar pressure. The resulting granulate, containing about 5% Polydextrose, was free flowing and suitable for direct compression.

Tablets were prepared as described in Example 3. Tablet hardness was 28 Strong Cobb Units. Tablet friability was 0.8%. Each tablet exhibited a good finish and was observed to have a pleasing sweetness and cooling sensation. A slight "dextrin" flavor was, however, noted.

Example 7

Production of a Directly Compressible Xylitol Granulate 6,000 g of xylitol milled to an average particle size of 50 microns was granulated with sodium carboxymethylcellulose utilizing 865.7 g of a 7% solids sodium carboxymethylcellulose (Aqualon 7L2P) in water as described for Example 3. The resulting granulate exhibited good flow characteristics. It had a bulk density of 0.41 g/ml and an average particle size of about 300 microns. Less than 15% passed through a 149 micron sieve. The granulate contained about 1% sodium carboxymethylcellulose and about 0.1% water.

Tablets were prepared as described in Example 3. The resulting tablets had a hardness of 24 Strong Cobb Units and a friability of 6.1%. Some capping was observed. Tablets were observed to have a pleasing sweetness and cooling sensation and had a good finish.

Example 8

Production of a Directly Compressible Xylitol Granulate 6,000 g of xylitol milled to an average particle size of 50 microns was granulated with sodium carboxymethylcellulose utilizing 2,651.4 g of a 7% solids sodium carboxymethylcellulose solution in water as described for Example 7. The resulting granulate exhibited good flow characteristics. It had a bulk density of 0.36 g/ml and an average particle size of about 500 microns. Less than 5% passed through a 149 micron sieve. The granulate contained about 3% sodium carboxymethylcellulose and about 0.3% water.

Tablets were prepared as described in Example 3. The resulting tablets had a hardness of greater than 40 Strong Cobb Units and 0.0% friability. No capping or lamination was observed. Tablets further exhibited a pleasing sweetness and cooling sensation and had a good finish. It was noted, however, that the tablets had a slight yellow/orange cast.

Example 9

Production of a Directly Compressible Xylitol Granulate 6,000 g of xylitol milled to an average particle size of 90 microns was granulated with sodium carboxymethylcellulose utilizing 1,305.7 g of a 7% solids sodium carboxymethylcellulose solution in water as described for Example 7. The resulting granulate exhibited good flow characteristics. It had a bulk density of 0.44 g/ml and an average particle size of about 450 microns. Less than 5% passed through a 177 micron sieve. The granulate contained about 1.5% sodium carboxymethylcellulose and about 0.3% water.

Tablets were prepared as described in Example 3. The resulting tablets had a hardness of 14 Strong Cobb Units and a friability of less than 1%. No capping or lamination was observed. The tablets were observed to have a pleasing sweetness and cooling sensation and had a good finish. No off color was observed.

Example 10

Production of a Directly Compressible Xylitol Tablet 500 grams of milled 50 micron xylitol was sieved into a blender and mixed as in Example 1. A 50% solution of FINMALT L (a hydrogenated starch hydrolysate available from Cultor Ltd., Finland) was added and a granulate was produced as in Example 1. The resulting granulate consisted of about 97% by weight xylitol and about 3% by weight hydrogenated starch hydrolysate.

The granulate was formed into tablets as in Example 1. The tablets exhibited hardness of between about 10 and 11 Strong Cobb units. Each tablet was observed to have a good finish and exhibited a pleasing sweetness and cooling effect.

The foregoing general discussion and experimental examples are intended to be illustrative of the present invention, and are not to be considered limiting. Other variations within the spirit and scope of this invention are possible and will present themselves to those skilled in the art.

We claim:

1. A directly compressible, non-cariogenic free flowing xylitol granulate having an average particle size of up to about 500 microns in which the sensorial properties of xylitol are not noticeably diminished which consists of xylitol and a physiologically acceptable, non-cariogenic binder in the range of about 0.1% to about 5% by weight taken from the group consisting of polymerized reducing sugars, alkali carboxymethylcellulose and hydrogenated starch hydrolysate.

2. The directly compressible granulate of claim 1 wherein said polymerized reducing sugar is polydextrose.

3. The directly compressible granulate of claim 2 wherein said polydextrose is in a partially purified or purified, and/or partially neutralized or neutralized form.

4. The directly compressible granulate of claim 2 wherein said polydextrose is present in the range of about 0.5% to about 5% by weight.

5. The directly compressible granulate of claim 4 wherein said polydextrose is present in an amount of about 3% by weight.

6. The directly compressible granulate of claim 1 wherein said alkali carboxymethylcellulose is sodium carboxymethylcellulose.

7. The directly compressible granulate of claim 6 wherein said sodium carboxymethylcellulose is present in the range of about 0.5% to about 3% by weight.

8. The directly compressible granulate of claim 7 wherein said sodium carboxymethylcellulose is present in an amount of about 1.5% by weight.

9. The directly compressible granulate of claim 1 wherein said hydrogenated starch hydrolysate is present in an amount of about to about 5% by weight.

10. The directly compressible granulate of claim 9 wherein said hydrogenated starch hydrolysate is present in an amount of about 3% by weight.

11. The directly compressible granulate of claim 1 which additionally includes an intense sweetener.

12. The directly compressible granulate of claim 11 wherein said intense sweetener is taken from the group consisting of dipeptide sweeteners, saccharin, acesulfame K, stevioside, cyclamate, neohesperidin dihydrochalcone and sucralose.

13. A relatively stable, non-cariogenic consumable tablet formed by direct compression means which exhibits a noted cooling effect when consumed which is sweetened by a sweetener composition consisting essentially of xylitol in the range of about 95% to about 99.9% by weight, and a physiologically acceptable, non-cariogenic binder which does not noticeably affect the sensorial properties of xylitol in the range of about 0.1% to about 5% by weight taken from the group consisting of polymerized reducing sugars, alkali carboxymethylcellulose and hydrogenated starch hydrolysate, wherein said tablet exhibits hardness of at least 10 Strong Cobb Units and friability of less than about 3% as calculated by the percentage (by weight) of powder or broken pieces measured after tablets are dropped by means of replicate revolutions through the diameter of the rotating plexiglass drum of a friabilator.

14. The consumable tablet of claim 13 wherein said tablet exhibits hardness of at least 15 Strong Cobb Units, and a friability of less than about 1%.

15. The consumable tablet of claim 13 wherein said polymerized reducing sugar is polydextrose.

16. The consumable tablet of claim 15 wherein said polydextrose is in a partially purified or purified, and/or partially neutralized or neutralized form.

17. The consumable tablet of claim 15 wherein said sweetener composition is comprised of xylitol in the range of about 97% to about 99.5% by weight, and polydextrose in the range of about 0.5% to about 3% by weight.

18. The consumable tablet of claim 17 wherein said sweetener composition comprises about 97% xylitol and about 3% polydextrose by weight.

19. The consumable tablet of claim 13 wherein said alkali carboxymethylcellulose is sodium carboxymethylcellulose.

20. The consumable tablet of claim 19 wherein said sweetener composition comprises xylitol in the range of about 97% to about 99.5% by weight, and sodium carboxymethylcellulose in the range of about 0.5% to about 3% by weight.

21. The consumable tablet of claim 20 wherein said hardness is greater than about 10 Strong Cobb Units and said friability is less than about 1%.

22. The consumable tablet of claim 13 wherein said sweetener composition comprises about 95% to about 99% by weight xylitol, and about 0.1% to about 5% hydrogenated starch hydrolysate by weight.

23. The consumable tablet of claim 22 wherein said sweetener composition comprises about 97% xylitol and about 3% hydrogenated starch hydrolysate by weight.

24. The consumable tablet of claim 13 which additionally includes an intense sweetener.

25. The consumable tablet of claim 24 wherein said intense sweetener is taken from the group consisting of dipeptide sweeteners, saccharin, acesulfame K, stevioside, cyclamate, neohesperidin dihydrochalcone and sucralose.

26. A method of production for a directly compressible, non-cariogenic free flowing xylitol granulate having an average particle size of up to about 500 microns which exhibits a cooling affect when consumed which consists of granulating, by means which simultaneously mix and dry the constituents, milled xylitol with an average particle size of between 40–180 microns with a physiologically acceptable, non-cariogenic binder in an aqueous solution wherein said binder does not noticeably affect the sensorial properties of xylitol, said binder taken from the group consisting of polymerized reducing sugars present in solution in an amount of less than 15% by weight on a dry basis, carboxymethylcellulose present in solution in an amount less than 10% by weight dry substance and hydrogenated starch hydrolysate present in solution in an amount of less than 20% by weight on a dry basis, with said binder present in an amount in the range of about 0.5% to 5% by weight to produce a free flowing granulate; and screening the resulting granulate.

27. The method of claim 26 wherein said polymerized reducing sugar is polydextrose.

28. The method of claim 27 wherein said polydextrose is in a partially purified or purified and/or partially neutralized or neutralized form.

29. The method of claim 27 wherein said polydextrose is present in an amount of about 3% by weight.

30. The method of claim 26 wherein said alkali carboxymethylcellulose is sodium carboxymethylcellulose.

31. The method of claim 30 wherein said sodium carboxymethylcellulose is present in the range of about 0.5% to about 3%.

32. The method of claim 31 wherein said sodium carboxymethylcellulose is present in an amount of about 1.5% by weight.

33. The method of claim 26 wherein said hydrogenated starch hydrolysate is present in the range of about 1% to about 5% by weight.

34. The method of claim 33 wherein said hydrogenated starch hydrolysate is present in an amount of about 3% by weight.

35. The method of claim 26 wherein said milled xylitol has an average particle size of between about 40 to about 120 microns.

36. The method of claim 35 wherein said milled xylitol has an average particle size of between about 50 to about 90 microns.

37. A directly compressible granulate which comprises a physiologically acceptable polyol selected from the group consisting of mannitol, lactitol, sorbitol, isomalt, maltitol or a sweetener with a glycemic index of less than about 50 such as crystalline fructose, and combinations thereof, and polydextrose in the range of about 0.1% to about 5% weight.

* * * * *